United States Patent
von Oepen

(10) Patent No.: US 6,652,573 B2
(45) Date of Patent: *Nov. 25, 2003

(54) RADIAL EXPANSIBLE STENT FOR IMPLANTING IN BODY VESSELS

(75) Inventor: Randolf von Oepen, Hirrlingen (DE)

(73) Assignee: Jomed GmbH, Rangendingen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/312,083

(22) Filed: May 15, 1999

(65) Prior Publication Data

US 2002/0151959 A1 Oct. 17, 2002

(30) Foreign Application Priority Data

May 16, 1998 (DE) .......................... 198 22 157

(51) Int. Cl.⁷ .................................................. A61F 2/06
(52) U.S. Cl. .................................................... 623/1.15
(58) Field of Search ................... 606/181, 191, 606/195, 198, 108; 623/1, 1.12, 1.13, 1.15, 12

(56) References Cited

U.S. PATENT DOCUMENTS

| | | | | |
|---|---|---|---|---|
| 5,697,971 A | * | 12/1997 | Fischell et al. ................. | 623/1 |
| 5,827,321 A | * | 10/1998 | Roubin et al. ............... | 606/195 |
| 5,843,175 A | * | 12/1998 | Frantzen ........................ | 623/1 |
| 5,855,600 A | * | 1/1999 | Alt ................................. | 623/1 |
| 6,068,656 A | * | 5/2000 | Von Oepen ................ | 623/1.17 |
| 6,190,403 B1 | * | 2/2001 | Fischell et al. ............ | 623/1.16 |

FOREIGN PATENT DOCUMENTS

DE     297 01 758.6     3/1997

* cited by examiner

Primary Examiner—Michael J. Milano
Assistant Examiner—Vy Q. Bui
(74) Attorney, Agent, or Firm—Michael J. Striker

(57) ABSTRACT

A radial expansible stent for implanting in a blood vessel in the region of a vessel branch has a hollow cylindrical element, and the hollow cylindrical element at least over a portion is provided with a plurality of radial openings having edges, the edges at least locally being strip-shaped and forming shaped formations.

22 Claims, 2 Drawing Sheets

RADIAL EXPANSIBLE STENT FOR IMPLANTING IN BODY VESSELS

BACKGROUND OF THE INVENTION

The present invention relates to a radial expansible stent for implantation in body vessels.

Stents as a rule are inserted after a vessel dialation in the vessel and expand there, so as to prevent a closure of the vessel. Such vessel closures can occur in the region of the vessel branches, and in some cases the total branch region must be secured after the expansion of the vessel. It is proposed for this purpose to insert a first stent in a main vessel and subsequently insert a second stent in the branching vessel through a radial opening of the first stent and expand the same. In order to make possible the insertion of the second stent through a radial opening of the first stent and to prevent excessive flow resistance in the branch region of the vessel for the blood, it is proposed in the German patent document DE 297 01 758 to use a stent which is provided locally with increased radial openings. In practice it has been however shown that these stents are not generally usable. In the region of the increased radial openings frequently the radial rigidity of the stent is not sufficient. Moreover, the covering degree of the vessel wall in the region of the increased openings is too low to prevent an entrainment of released vessel deposits from the vessel wall into the blood stream. These released deposits can lead, depending on the position of the vessel, to embolies, strokes, etc.

SUMMARY OF THE INVENTION

Accordingly, it is an object of the present invention to provide a stent for implantation in a body vessel, which avoids the disadvantages of the prior art.

In keeping with these objects and with others which will become apparent hereinafter, one feature of the present invention resides, briefly stated, in a stent for implantation in a body vessel, in particular in the region of a vessel branch, which has a hollow-cylindrical element, and the hollow cylindrical element has at least a portion with radial openings whose edges are at least locally strip-shaped and form one or several loops and/or bulges.

The loops and/or bulges can be dimensioned and arranged so that the diameter of the radial openings is increased so that the second, not expanded stent can pass through the radial openings easily, or is a radially expansible in the region of the openings. It is possible since that the loops or bulges during passage or expansion of the second stent are pulled from one another, and therefore the cross-section area of the openings is substantially increased.

Those radial openings through which no second stent is passed, have however either the same cross-sectional size as the radial openings in another portion of the stent, or a slightly increased diameter relative to them. Thereby a sufficient radial stability as well as a sufficient covering degree of the vessel wall is guaranteed, to reliably prevent the entrainment of deposits released from the vessel wall into the blood flow.

The radial rigidity of the stent can be adjusted at least in one portion so that it corresponds at least approximately to the radial rigidity in the remaining portions.

In accordance with a preferable embodiment, the stent is provided over the half of its length with the radial openings, whose edges are formed at least locally strip-shaped and form at least one or several loops and/or bulges. The placing of the first stent with such a device is relatively simple, since it is provided over a relatively great length with the specially designed radial openings.

The inventive stent can be preferably formed of a massive tube by laser cutting or the like.

Further advantages are provided when it is composed of a material which is well visible during an x-ray radiation or provided with coating of such a material. As possible materials, gold or platinum can be for example utilized.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
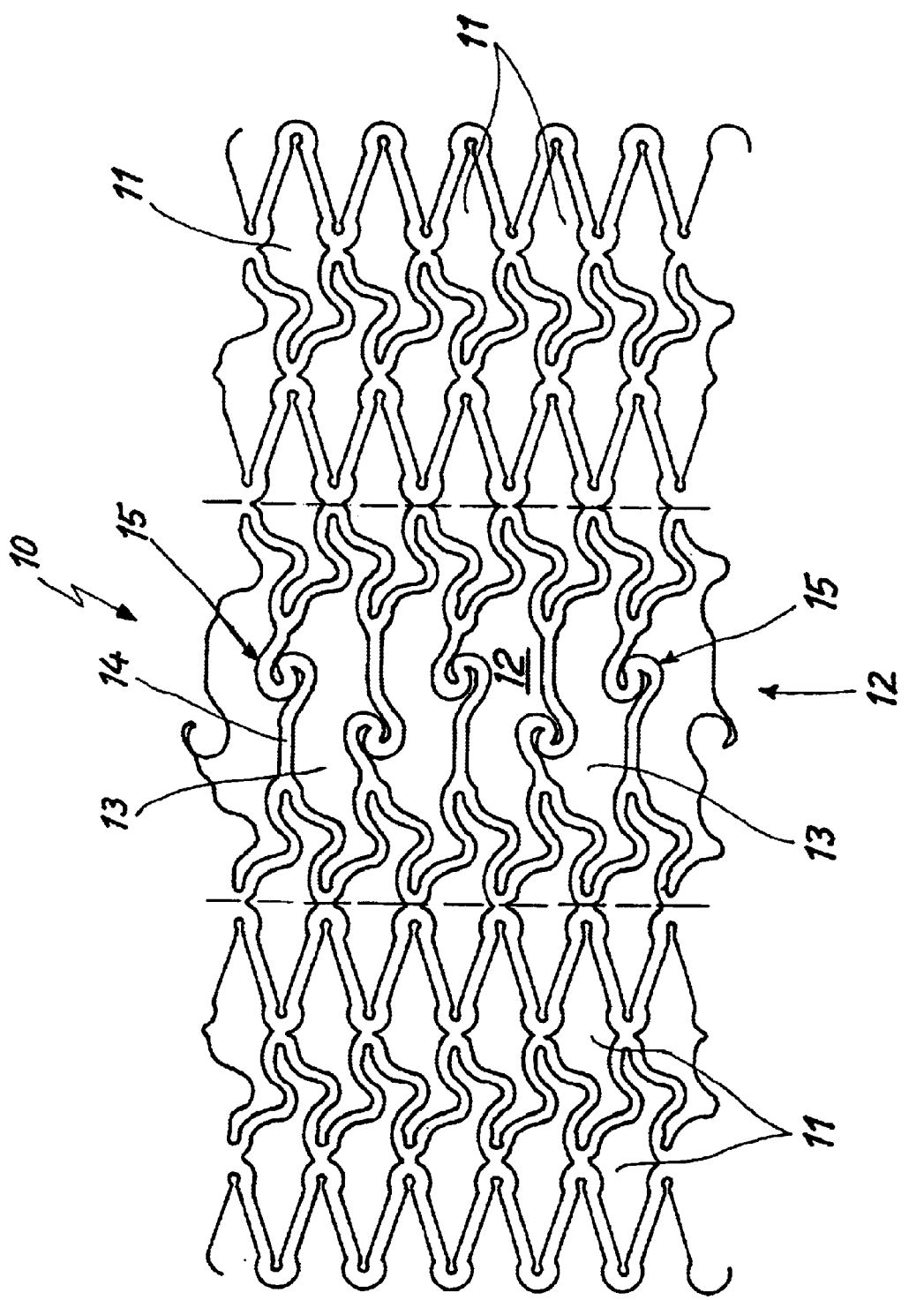
FIG. 1 is a view showing a surface structure of a stent in accordance with the present invention.

A stent in accordance with the present invention is identified as a whole with reference numeral 10. FIG. 1 shows a portion of the surface of the stent 10. As can be seen from the drawings, the stent is provided with a plurality of substantially rhombus-shaped openings 11 distributed over its periphery. Radial openings 13 are provided in a central region 12 of the stent, which extends between the dashed lines shown in FIG. 1. Their cross-sectional surface is slightly greater than the cross-sectional surface of the other radial openings 11. The radial openings 13, as well as the radial openings 11 are enclosed by strip-shaped edges 14. The edges 14 of the radial openings 13 have S-shaped loops 15. As a result it is possible to increase the openings 13 with regarding to their cross-sectional area.

The stent 10 is suitable thereby for placing in the region of vessel branches. A second stent can be easily introduced through the openings 13 by folding of the S-shaped loops 15 and then is radially expanded. Thereby the stent does not affect the blood flow through the vessel. Also, when the branching vessel must not be provided with a stent, one of the radial openings 13 can be expanded in its diameter, so that an unobjectionable blood flow is possible in a neighboring vessel. A displacement of the stent 10 in the vessel is provided relatively simply since the openings 13 extend over the whole stent periphery in the region 12.

Figure 2:
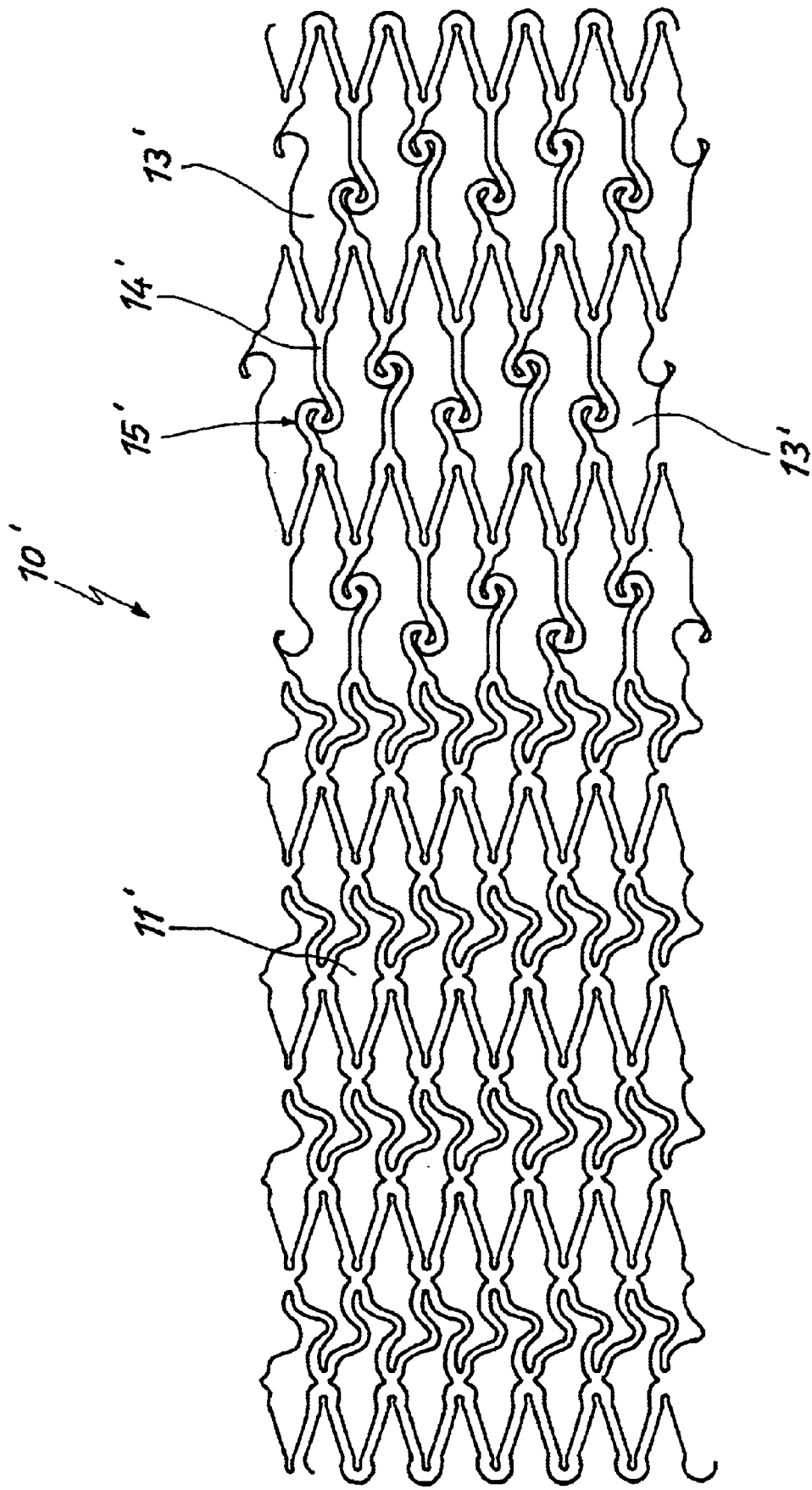
FIG. 2 is a view showing a surface structure of a stent in accordance with another embodiment of the present invention.

In contrast to the stent 10, FIG. 2 shows another embodiment of a stent which is identified with reference numeral 10'. In the stent 10' radial openings 13' with edges 14' are provided not only in a central region, but also over one of its halves. The openings 13' have edges 14' in which S-shaped loops 15' are formed. With this design of the stent 10', the placing inside the vessel in a branch region is simplified.

Both stents 10 and 10' have the advantage that they provide a very good covering degree of the vessel wall and still allow a very significant expansion of individual radial openings for passage of a second stent. The high covering degree of the blood vessel ensures that no deposits are released at the vessel wall and can be entrained in the blood flow. On the other hand, the radial rigidity of the stents 10 and 10' also in the region of the radial openings 13' is as high as in the region of the radial openings 11, 11'. Instead of the S-shaped loops 15, 15', naturally also meandering loops, bulges and similar structures can be provided in the edges 14, 14'.

It will be understood that each of the elements described above, or two or more together, may also find a useful application in other types of constructions differing from the types described above.

While the invention has been illustrated and described as embodied in radial expansible stent for implanting in body vessels, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A radially expandable stent for implanting in a blood vessel in the region of a vessel branch, the stent comprising:
   a first plurality of cells forming a first plurality of radial openings; and
   a second plurality of cells forming a second plurality of radial openings,
   wherein each of said first plurality of radial openings is larger than each of said second plurality of radial openings, and
   wherein said first plurality of cells comprises a radial strength that is at least approximately equal to a radial strength of said second plurality of cells.

2. A radially expandable stent as defined in claim 1, wherein each of said first plurality of radial openings is configured for expansion to a first expanded width that is greater than a second expanded width to which each of said second plurality of radial openings is configured for expansion.

3. A radially expandable stent as defined in claim 2, wherein each of said first plurality of radial openings is configured to expand in isolation to the first expanded width upon expansion of a second stent therein.

4. A radially expandable stent as defined in claim 2, wherein said first expanded width is configured for passage of a second stent therethrough.

5. A radially expandable stent as defined in claim 2, wherein said first expanded width is configured for expansion of a second stent therein.

6. A radially expandable stent as defined in claim 1, wherein said first plurality of radial openings comprises edges having shaped formations.

7. A radially expandable stent as defined in claim 6, wherein said edges are strip-shaped.

8. A radially expandable stent as defined in claim 6, wherein said shaped formations of said edges comprise a shape chosen from the group consisting of bulges, meandering loops, S-shaped loops, and loops.

9. A radially expandable stent as defined in claim 1, wherein the stent is formed by laser cutting.

10. A radially expandable stent as defined in claim 1, wherein the stent comprises a material visible during X-Ray radiation.

11. A radially expandable stent as defined in claim 10, wherein the material is chosen from the group consisting of gold and platinum.

12. A radially expandable stent as defined in claim 1, wherein the second plurality of radial openings are substantially rhombus-shaped.

13. A radially expandable stent as defined in claim 1, wherein the first plurality of radial openings are disposed over at least a half of length of the stent.

14. A radially expandable stent as defined in claim 1, wherein the first plurality of radial openings are disposed over at least a central region of the stent.

15. A radially expandable stent as defined in claim 1, wherein said first plurality of radial openings are disposed over at least an end of the stent.

16. The radially expandable stent as defined in claim 1, wherein said radial strength of said first plurality of cells is equal to said radial strength of said second plurality of cells.

17. A radially expandable stent for implanting in a blood vessel in the region of a vessel branch, the stent comprising:
    a first plurality of radial openings having edges with shaped formations; and
    a second plurality of radial openings,
    wherein said first plurality of radial openings is formed by a first plurality of cells and said second plurality of radial openings is formed by a second plurality of cells, each of said first plurality of radial openings being larger than each of said second plurality of radial openings and the radial strength of said first plurality of cells being at least approximately equal to the radial strength of said second plurality of cells,
    wherein said first plurality of radial openings are disposed over at least an end of the stent, and
    wherein said shaped formations of said edges comprise a loop shape that is doubled over and forms an opening.

18. A radially expandable stent as defined in claim 17, wherein said loop shape of said shaped formations further comprises a shape chosen from the group consisting of bulges, meandering loops, and S-shaped loops.

19. The radially expandable stent as defined in claim 17, wherein said radial strength of said first plurality of cells is equal to said radial strength of said second plurality of cells.

20. A radially expandable stent for implanting in a blood vessel in the region of a vessel branch, the stent comprising:
    a first plurality of radial openings comprising edges having shaped formations that double over and form an opening; and
    a second plurality of radial openings,
    wherein said first plurality of radial openings is formed by a first plurality of cells and said second plurality of radial openings is formed by a second plurality of cells, each of said first plurality of radial openings being larger than each of said second plurality of radial openings and the radial strength of said first plurality of cells being at least approximately equal to the radial strength of said second plurality of cells,
    wherein each of said first plurality of radial openings is configured for expansion to a first expanded width that is greater than a second expanded width to which each of said second plurality of radial openings is configured for expansion, wherein each of said first plurality of radial openings is configured to expand in isolation to the first expanded width upon expansion of a second stent therein, and wherein said first plurality of radial openings are disposed over at least an end of the stent.

21. A radially expandable stent as defined in claim 20, wherein said shaped formations of said edges comprise a shape chosen from the group consisting of bulges, meandering loops, S-shaped loops, and loops.

22. The radially expandable stent as defined in claim 20, wherein said radial strength of said first plurality of cells is equal to said radial strength of said second plurality of cells.

* * * * *